United States Patent
Kravtchenko et al.

(10) Patent No.: US 7,776,104 B2
(45) Date of Patent: Aug. 17, 2010

(54) OXIDIZING COMPOSITION COMPRISING INSOLUBLE COMPOUNDS, AND PROCESSES USING THIS COMPOSITION

(75) Inventors: Sylvain Kravtchenko, Shanghai (CN); Claude Dubief, Le Chesnay (FR)

(73) Assignee: L'Oreal S.A., Paris (FR)

( * ) Notice: Subject to any disclaimer, the term of this patent is extended or adjusted under 35 U.S.C. 154(b) by 8 days.

(21) Appl. No.: 11/509,022

(22) Filed: Aug. 24, 2006

(65) Prior Publication Data

US 2007/0044252 A1 Mar. 1, 2007

(30) Foreign Application Priority Data

Aug. 25, 2005 (FR) .................. 05 08754

(51) Int. Cl.
*A61Q 5/10* (2006.01)
(52) U.S. Cl. ............... 8/405; 8/406; 8/435; 8/512; 8/552; 8/580; 8/582
(58) Field of Classification Search ................ 8/405, 8/406, 435, 512, 552, 580, 582
See application file for complete search history.

(56) References Cited

U.S. PATENT DOCUMENTS

| | | | |
|---|---|---|---|
| 3,193,464 A | 7/1965 | Edman et al. | |
| 4,003,699 A | 1/1977 | Rose et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Löwe et al. | |
| 5,865,853 A | 2/1999 | Schmitt et al. | |
| 6,099,592 A | 8/2000 | Vidal et al. | |
| 6,238,653 B1 | 5/2001 | Narasimhan et al. | |
| 6,254,647 B1 | 7/2001 | Fröhling | |
| 6,277,154 B1 | 8/2001 | Lorenz | |
| 6,284,003 B1 | 9/2001 | Rose et al. | |
| 6,312,674 B1 * | 11/2001 | Maubru et al. | 424/62 |
| 6,540,791 B1 * | 4/2003 | Dias | 8/111 |
| 6,730,789 B1 | 5/2004 | Birault et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,060,110 B2 | 6/2006 | Vidal et al. | |
| 7,077,873 B2 | 7/2006 | David et al. | |
| 7,217,298 B2 | 5/2007 | Legrand et al. | |
| 7,261,743 B2 | 8/2007 | Plos et al. | |
| 2002/0046431 A1 | 4/2002 | Laurent et al. | |
| 2003/0084516 A9 | 5/2003 | Kravtchenko et al. | |
| 2003/0106169 A1 | 6/2003 | Vidal et al. | |
| 2004/0200009 A1 | 10/2004 | Vidal | |
| 2005/0081311 A1 | 4/2005 | Schmenger et al. | |
| 2005/0232953 A1 | 10/2005 | Barnikol et al. | |

FOREIGN PATENT DOCUMENTS

| | | |
|---|---|---|
| DE | 0 709 932 | 8/1941 |
| DE | 23 59 399 | 6/1975 |
| DE | 24 32 614 | 1/1976 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 715 842 | 6/1996 |
| EP | 0 770 375 | 5/1997 |
| EP | 0 823 250 | 2/1998 |
| EP | 1 048 289 | 11/2000 |
| EP | 1 438 951 | 7/2004 |
| FR | 2 733 749 | 11/1996 |
| FR | 2 801 308 | 5/2001 |
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 844 269 | 3/2004 |
| GB | 1 026 978 | 4/1966 |
| GB | 1 153 196 | 5/1969 |
| JP | 53-95693 | 8/1978 |

(Continued)

OTHER PUBLICATIONS

Isopropyl myristate document (no dated).*

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

A ready-to-use oxidizing composition for treating keratin materials, such as human keratin fibers, in particular the hair, comprising, in a cosmetically acceptable medium: (a) at least one oxidizing agent, (b) at least 30% by weight of at least one water-insoluble oxygenated organic no-dyeing particular compound relative to the total weight of the said composition, and (c) at least 20% by weight of water relative to the total weight of the said composition, and to processes for bleaching, stripping, dyeing, lightening or permanently reshaping human keratin fibers and in particular the hair, and also to the use of the said composition for bleaching, stripping, dyeing, lightening and permanently reshaping human keratin fibers and in particular the hair.

22 Claims, No Drawings

FOREIGN PATENT DOCUMENTS

| | | |
|---|---|---|
| JP | 55-22638 | 2/1980 |
| JP | 02-19576 | 1/1990 |
| JP | 05-163124 | 6/1993 |
| JP | 2004-26703 | 1/2004 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/078660 | 10/2002 |
| WO | WO 02/100369 | 12/2002 |
| WO | WO 02/100834 | 12/2002 |
| WO | WO 03/105797 | 12/2003 |
| WO | WO 2005/074871 | 8/2005 |
| WO | WO 2005/074873 | 8/2005 |

OTHER PUBLICATIONS

Copending U.S. Appl. No. 11/509,023, filed Aug. 24, 2006.
Copending U.S. Appl. No. 11/509,010, filed Aug. 24, 2006.
French Search Report for FR 05/08753 (copending U.S. Appl. No. 11/509,023), dated May 12, 2006.
French Search Report for FR 05/08754 (present application), dated May 12, 2006.
French Search Report for FR 05/08755 (copending U.S. Appl. No. 11/509,010), dated May 12, 2006.
"The Science of Hair Care", Edited by Charles Zviak, Marcel Dekker Inc., 1986.
English language abstract of DE 24 32 614, Jan. 22, 1976.
English language abstract of EP 0 770 375, May 2, 1997.
English language abstract of EP 1 048 289, Nov. 2, 2000.
English language abstract of JP 53-095693, Aug. 22, 1978.
English language abstract of JP 55-022638, Feb. 18, 1980.
English language abstract of JP 02-019576, Jan. 23, 1990.
English language abstract of JP 05-163124, Jun. 29, 1993.
English language abstract of JP 2004-026703, Jan. 29, 2004.
English language abstract of WO 2005/074871, Aug. 18, 2005.
English language abstract of WO 2005/074873, Aug. 18, 2005.
Office Action mailed Dec. 23, 2008, in co-pending U.S. Appl. No. 11/509,023.
Office Action mailed Feb. 11, 2009, in co-pending U.S. Appl. No. 11/509,010.
Office Action mailed Jun. 18, 2008, in co-pending U.S. Appl. No. 11/509,010.
Office Action mailed Jun. 19, 2008, in co-pending U.S. Appl. No. 11/509,023.
Office Action mailed Aug. 27, 2009, in co-pending U.S. Appl. No. 11/509,023.
Office Action mailed Dec. 23, 2008, in co-pending U.S. Appl. No. 11/509,023.
Office Action mailed Feb. 11, 2009, in co-pending U.S. Appl. No. 11/509,010.
Office Action mailed Jun. 18, 2008, in co-pending U.S. Appl. No. 11/509,010.
Office Action mailed Jun. 19, 2008, in co-pending U.S. Appl. No. 11/509,023.

* cited by examiner

OXIDIZING COMPOSITION COMPRISING INSOLUBLE COMPOUNDS, AND PROCESSES USING THIS COMPOSITION

This application claims benefit of priority under 35 U.S.C. §119 to French Patent Application No. FR 05 08754, filed Aug. 25, 2005, the contents of which are also incorporated herein by reference.

The present disclosure relates to ready-to-use oxidizing compositions for treating keratin fibers, comprising a water-insoluble compound, and processes for bleaching or stripping, dyeing, lightening or permanently reshaping human keratin fibers such as the hair, and the use of the ready-to-use composition for bleaching, stripping, dyeing, lightening or permanently reshaping the keratin fibers.

Oxidizing compositions are used to lighten or bleach keratin fibers. For instance, the bleaching or lightening of the hair may be obtained by oxidation of the melanin pigments, this oxidation possibly leading in the extreme case to the dissolution and total removal of these pigments.

The aim of bleaching is generally two-fold. The bleaching process may either be carried out simply to give the hair a lighter appearance, or to prepare it for the application of a dye product (direct or oxidation dye), the resulting shade generally being lighter than the natural shade.

It is known practice to bleach the hair with pastes (or poultices) applied directly to the hair and obtained by mixing, at the time of use, a bleaching composition based on peroxide derivatives (oxidizing agents) with water or, more usually, with aqueous hydrogen peroxide solution. The bleaching composition comprises, in a known manner, a peroxide derivative, generally a sodium, potassium or ammonium persulfate or perborate and occasionally a percarboxylic acid salt or a peroxide, for example of barium, strontium, urea or melanin. Usually, these compositions also comprise, in a known manner, strongly alkaline agents, such as alkali metal or alkaline-earth metal metasilicates, phosphates or carbonates (pH regulators). Finally, they may optionally comprise other additives or adjuvants that are standard in the field: agents for controlling the release of oxygen into the mixture with aqueous hydrogen peroxide solution, thickeners, such as cellulose derivatives (for example carboxymethylcellulose) or starch and derivatives thereof, or alternatively guar gum, xanthan gum and alginates; surfactants, such as anionic surfactants (for instance alkyl sulfates); sequestrants; and fragrances. Such bleaching compositions are described, for example, in "The Science of Hair Care" by C. Zviak, Marcel Dekker Inc. 1986, pages 225-226.

The bleaching compositions may also result from the mixing, at the time of use, of the anhydrous powder of a peroxygenated reagent with an aqueous composition comprising the alkaline compounds and another aqueous composition comprising hydrogen peroxide.

The fiber bleaching process generally lasts between 20 minutes and 1 hour. This leave-on time varies according to the form of the oxidizing composition (cream, shampoo, powder, solution or emulsion), according to the desired level or degree of lightening, and according to the concentration of the reagents of the ready-to-use oxidizing composition, i.e., the amount of alkaline compounds and of peroxygenated reagents, the volume of aqueous hydrogen peroxide solution or the proportion of reinforcing powders.

It has been sought for a long time to accelerate the process of bleaching or lightening of keratin fibers and to increase the degree of lightening of the fibers, i.e., to lighten them more.

With the aim of reducing the leave-on time, it would be tempting to increase the proportion of reagents in the oxidizing composition. However, a higher concentration of components may lead to greater impairment of the keratin fibers, or even to irritation or dermatitis of the scalp or to the appearance of stinging.

Oxidizing compositions are also used in permanent-reshaping processes, as fixing compositions for reconstructing the fibers in the desired shade.

In the course of a hair permanent-reshaping process, the hair is wound up on rollers and is then impregnated with a reducing composition, referred to as a curling composition, which is left to act for between 5 minutes and 1 hour depending on the nature of the hair and the reducing agent that is used. The shape of the hair is then fixed using an oxidizing composition, which is applied over about 5 minutes and then left to activate for about 5 to 30 minutes. After unwinding the locks, the oxidizing composition is applied to the ends over about 5 minutes and is then left to act for about 5 minutes. Finally, the treated hair is rinsed. This standard permanent-reshaping process is long and laborious.

As for the bleaching process, it would be desirable to develop a more efficient oxidizing composition leading to a shorter leave-on time, and thus reducing the duration of the permanent-reshaping process.

Thus there is a need for oxidizing compositions for bleaching or for permanent reshaping that are more efficient, i.e. that react more quickly with the structure of the fiber, while at the same time being as harmless as possible with respect to the fibers and the scalp.

In the context of oxidation dyeing, a composition comprising at least one oxidation dye is generally mixed, at the time of use, usually at alkaline pH, with at least one oxidizing composition generally based on aqueous hydrogen peroxide solution formulated at acidic pH. The mixture obtained is applied to the head with a leave-on time that may be up to one hour. In the case of indirect lightening dyeing, the at least one oxidation dye is replaced with at least one direct dye.

There is a need to accelerate the dyeing process and/or to reduce the concentration of aqueous hydrogen peroxide solution in order to limit the impairment of the keratin fibers.

After considerable research conducted in this matter, the present inventors have discovered, surprisingly, that it is possible to obtain more efficient ready-to-use oxidizing compositions that show good harmlessness, while at the same time conserving the proportions of the reagents of the usual oxidizing compositions. These ready-to-use oxidizing compositions do not have at least one of the above-mentioned drawbacks.

The present disclosure also relates to processes for bleaching, stripping, oxidation dyeing, lightening and permanently reshaping keratin fibers, where the ready-to-use compositions may be used for bleaching, stripping, dyeing, lightening or permanently reshaping the fibers and to multi-compartment dyeing devices or "kits."

Other characteristics, aspects, and advantages of the present disclosure, featured in the description below, will allow the disclosure to be understood more clearly.

One aspect of the present disclosure is a ready-to-use oxidizing composition for treating keratin fibers, such as human keratin fibers, for instance the hair, comprising, in a cosmetically acceptable medium:

(a) at least one oxidizing agent, (b) at least 30% by weight of at least one water-insoluble oxygenated organic non-dyeing particular compound relative to the total weight of the composition, and (c) at least 20% by weight of water relative to the total weight of the composition.

The at least one oxidizing agent may be chosen from hydrogen peroxide and compounds capable of producing hydrogen peroxide via hydrolysis, such as urea peroxide, alkali metal bromates, persalts such as perborates, persulfates, percarbonates and peroxides of alkali metals or alkaline-earth metals, for instance sodium, potassium or magnesium, and peracids, or mixtures thereof; and oxidase enzymes, among which mention may be made of 2-electron oxidoreductases such as uricases and 4-electron oxygenases, for instance laccases, where appropriate in the presence of the appropriate substrate thereof. For instance, hydrogen peroxide may be used.

The amount of oxidizing agent in the ready-to-use composition ranges from 2% to 35% by weight of the ready-to-use composition, for instance ranging from 5% to 30% by weight of the ready-to-use composition.

For the purposes of the present disclosure, the term "oxygenated organic compound" means any organic compound comprising at least one oxygen atom in its elementary molecular structure.

According to the present disclosure, the term "water-insoluble" means compounds having a solubility in water at room temperature (25° C.) of less than 0.5% by weight.

The at least one oxygenated organic compounds of the present disclosure may be polymeric or non-polymeric compounds.

The polymeric insoluble oxygenated organic compounds according to the present disclosure may be chosen from polyamides 6, 66 and 11, polyesters, polyurethanes, polycyanoacrylates, polymethyl methacrylates, polycarbonates, Teflon (polytetrafluoroethylene) and silicone resins or elastomers.

The non-polymeric oxygenated organic compounds of the present disclosure may be chosen from fatty alcohols and fatty acid or fatty alcohol esters, amides or ethers. Among the fatty acid or fatty alcohol esters, amides and ethers, non-limiting mention may be made of the fatty chains of fatty acids or fatty alcohols containing from 8 to 40 carbon atoms, which are optionally hydroxylated. Among the fatty alcohols, non-limiting mention may be made of fatty alcohols containing from 8 to 40 carbon atoms. Non-limiting examples that may be mentioned include: ethylene glycol monostearate and distearate, pentaerythrityl monooleate, sorbitan tristearate, glyceryl dioleate, fatty esters, amides and ethers of ethylene glycol or of propylene glycol, distearyl ether, stearyl alcohol, behenyl alcohol and cetylstearyl alcohol.

The amount of water-insoluble compound in the ready-to-use composition is greater than 30% by weight of the ready-to-use oxidizing composition, for instance ranging from 30% to 75% by weight of the ready-to-use oxidizing composition, for example 30% to 60% by weight of the ready-to-use oxidizing composition.

Thus, when the at least one water-insoluble compound, as disclosed herein, is solid, the composition is in the form of a suspension. When the at least one water-insoluble compound according to the present disclosure is in liquid form, for example in the form of an organic phase that is insoluble in the aqueous phase, the composition is an emulsion, or even a dispersion.

The ready-to-use oxidizing composition according to the present disclosure comprises at least 20% by weight, for instance ranging from 20% to 78%, for example from 30% to 60% by weight of water relative to the total weight of the composition.

The ready-to-use oxidizing composition may also comprise at least one organic solvent.

The medium that is suitable for the compositions of the present disclosure is a cosmetic medium comprising water or a mixture of water and of at least one organic solvent. Organic solvents that may be mentioned include but are not limited to $C_1$-$C_4$ lower alkanols, such as ethanol and isopropanol; polyols and polyol ethers, for instance 2-butoxy-ethanol, propylene glycol, glycerol, propylene glycol monomethyl ether and diethylene glycol monomethyl ether and monoethyl ether, and also aromatic alcohols, for instance benzyl alcohol or phenoxyethanol, and mixtures thereof.

The solvents are present in proportions ranging from about 1% to 40% by weight, for example from about 5% to 30% by weight relative to the total weight of the dye composition.

The oxidizing composition according to the present disclosure may also comprise surfactants, thickening polymers or amphiphilic polymers to stabilize the dispersions, when the composition is in dispersion form.

These are conventionally used raw materials. Non-limiting examples include:
- anionic, nonionic, cationic and amphoteric surfactants comprising at least one linear or branched $C_6$-$C_{22}$ alkyl chain,
- amphiphilic polymers, for instance water-soluble or water-dispersible amphiphilic block copolymers, associative polymers bearing on their main chain oxyethylenated or non-oxyethylenated, telechelic or grafted $C_6$-$C_{22}$ alkyl and/or aryl groups, these polymers possibly being of cationic, anionic, amphoteric or nonionic charge,
- thickening polymers, for instance crosslinked acrylic polymers and natural or modified polysaccharides.

The ready-to-use oxidizing composition according to the present disclosure may also comprise additives conventionally used in the field, for instance sequestrants such as ethylenediaminetetraacetic acid, pentasodium pentetate (CTFA name) or etidronic acid; chemical hydrogen peroxide stabilizers such as alkali metal (for instance sodium or potassium) stannate and pyrophosphate salts, or sodium salicylate; fragrances; antifoams; cationic or amphoteric substantive polymers; water-soluble or water-insoluble conditioning polymers, or chelating agents.

Needless to say, a person skilled in the art will take care to select the optional additional compound(s) mentioned above, such that the properties of the ready-to-use oxidizing composition are not, or are not substantially, adversely affected by the envisaged addition(s).

The pH of the ready-to-use oxidizing composition according to the present disclosure may range from 2 to 12, for example, from 2.5 to 7 and further still, from 3 to 6.

The pH may be conventionally adjusted, if necessary, by adding basifying agents, for instance ammonia, monoethanolamine, diethanolamine, triethanolamine, isopropanolamine, 1,3-diaminopropane, an alkali metal or ammonium (bi)carbonate, an organic carbonate such as guanidine carbonate, or an alkaline hydroxide, all these compounds possibly being, of course, taken alone or as a mixture.

As stated above, the ready-to-use composition according to the present disclosure may result from the extemporaneous mixing of at least one anhydrous pulverulent composition with at least one organic composition.

For the purposes of the present disclosure, the term "bleaching" means the total or partial destruction of the natural pigments present in the keratin fibers (for instance eumelanins and phaeomelanins).

Another aspect of the present disclosure is also a process for bleaching human keratin fibers, such as the hair, which comprises applying the ready-to-use oxidizing composition according to the present disclosure to the area of wet or dry human keratin fibers to be bleached; leaving it to act for a leave-on the time that is sufficient to obtain the desired bleaching; removing the composition by rinsing with water, followed by washing with a shampoo, and then optionally drying.

The leave-on time may range from 1 to 60 minutes, for instance from 5 to 40 minutes.

For the purposes of the present disclosure, the term "stripping" means the total or partial destruction of the pigments or synthetic dyes present on or in the keratin fibers resulting from a direct or oxidation dyeing process.

The present disclosure also relates to a process for stripping human keratin fibers, such as dyed hair, which comprises applying the ready-to-use stripping composition according to the present disclosure to the area of wet or dry dyed human keratin fibers to be stripped; leaving it to act for a leave-on time that is sufficient to obtain the desired stripping; removing the composition by rinsing with water followed by washing with a shampoo, and then optionally drying.

In at least one embodiment, the leave-on time ranges from 1 to 60 minutes, for instance from 5 to 40 minutes.

Another aspect of the present disclosure is a process for the oxidation dyeing of human keratin fibers, for instance the hair, using a dye composition comprising, in a support that is suitable for dyeing keratin fibers, at least one oxidation dye precursor and a ready-to-use oxidizing composition as defined above. At the time of use, the ready-to-use oxidizing composition described is applied to the keratin fibers before or after applying the dye composition or mixed with this dye composition; the individual or mixed compositions are left to act for about 1 to 60 minutes, for example for about 5 to 40 minutes, followed by rinsing, washing with shampoo, optionally rinsing and finally drying. The individual dye compositions and oxidizing compositions described may be applied in any order, with or without intermediate rinsing.

The dye composition used in this dyeing process incorporates standard oxidation dye precursors such as oxidation bases chosen from phenylenediamines, bis(phenyl)alkylenediamines, para-aminophenols, ortho-aminophenols and heterocyclic bases, and the addition salts thereof; optionally combined with common couplers, for instance meta-phenylenediamines, meta-aminophenols, meta-diphenols, naphthalene-based couplers and heterocyclic couplers, and the addition salts thereof.

Another aspect of the present disclosure is a process for the lightening direct dyeing of human keratin fibers, such as the hair, using a dye composition comprising, in a support that is suitable for dyeing keratin fibers, comprising at least one direct dye and a ready-to-use oxidizing composition as defined above. At the time of use, the ready-to-use oxidizing composition as disclosed herein is applied to the keratin fibers before or after applying the dye composition or mixed with this dye composition; leaving the individual or mixed compositions to act for about 3 to 40 minutes, for example for about 5 to 30 minutes, followed by rinsing, washing with shampoo, optionally rinsing and finally drying. The individual dye compositions and oxidizing compositions described may be applied in any order, with or without intermediate rinsing.

The at least one direct dye used in this lightening direct dyeing process is a standard dye chosen from neutral, acidic or cationic nitrobenzene dyes, neutral, acidic or cationic azo direct dyes, neutral, acidic or cationic quinone, such as anthraquinone direct dyes, azine direct dyes, triarylmethane direct dyes, indoamine direct dyes and natural direct dyes.

Another aspect of the present disclosure is a process for treating human keratin fibers, such as the hair, in order to permanently reshape them, for instance in the form of permanent-waved hair, this process comprising the steps below.

A reducing composition is applied to the keratin fibers to be treated, the keratin fibers being placed under mechanical tension before, during or after the application of the reducing composition. This may be done lock by lock or all at once.

The hair onto which the reducing composition has been applied should conventionally be left with the composition on for a few minutes, generally five minutes to one hour. Thus, the reducing agent has time to act on the hair. For instance, this waiting phase may take place at a temperature ranging from 35° C. to 45° C., while the hair is also optionally protected with a bonnet.

The keratin fiber(s) impregnated with the reducing composition is optionally rinsed with an aqueous composition.

The ready-to-use oxidizing composition of the present disclosure is applied to the optionally rinsed keratin fiber(s), in order to fix the new shape given to the hair. Once again, the treated hair is left with the composition on for 3 to 20 minutes, for example for 5 to 10 minutes.

The keratin fibers are once again rinsed, generally with water.

Finally, an aspect of the present disclosure is multi-compartment devices, or "kits," for performing the processes as disclosed herein. For example, the present disclosure relates to a two-compartment device for dyeing, permanently reshaping or bleaching keratin fibers, such as human keratin fibers. A first compartment may comprise either at least one direct dye or at least one oxidation dye composition, or a reducing composition, or a first oxidizing composition, for instance comprising a peroxygenated salt, and a second compartment comprising the ready-to-use oxidizing composition defined above.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow illustrate the present disclosure without being limiting in nature.

EXAMPLES

Oxidizinq Composition:

| | |
|---|---|
| Distearyl ether | 35 g |
| Sodium lauryl sulfate | 2 g |
| Brij 700 | 1 g |
| Ammonium acryloyldimethyltaurate/Steareth 25 methacrylate crosspolymer | 2 g |

| -continued | |
|---|---|
| Sodium stannate hexahydrate | 0.04 g |
| EDTA | 0.02 g |
| Tetrasodium pyrophosphate decahydrate | 0.03 g |
| Hydrogen peroxide | 6 g |
| Phosphoric acid | qs pH 3 |
| Demineralized water | qs100 g |

This oxidizing composition was mixed at the time of use with a bleaching powder, Platine Precision®, that contained 50% persulfates, 24.1% silicates and 2.6% ammonium chloride, with a bleaching powder/oxidizing composition ratio equal to 1/1.5. The mixture obtained was applied to locks of chestnut-brown hair for 40 minutes. After rinsing, washing with a standard shampoo, rinsing again and drying, the locks showed very strong lightening power.

Similar results were obtained by replacing the distearyl ether weight-for-weight with the Nylon-6 powder sold by Inducthem under the name INDUCOS.

What is claimed is:

1. A ready-to-use oxidizing composition for treating keratin fibers, comprising, in a cosmetically acceptable medium:
   (a) at least one oxidizing agent;
   (b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
   (c) at least 20% by weight of water relative to the total weight of the composition.

2. The composition according to claim 1, wherein the at least one oxidizing agent is chosen from hydrogen peroxide, urea peroxide, alkali metal bromates, alkali metal or alkaline-earth metal perborates, persulfates, percarbonates or peroxides, and peracids, or mixtures thereof; and oxidase enzymes.

3. The composition according to claim 2, wherein the at least one oxidizing agent is hydrogen peroxide.

4. The composition according to claim 1, wherein the amount of the at least one oxidizing agent in the composition ranges from 2% to 35% by weight of the composition.

5. The composition according to claim 4, wherein the amount of the at least one oxidizing agent in the composition ranges from 5% to 30% by weight of the composition.

6. The composition according to claim 1, wherein the at least one water-insoluble oxygenated organic compound is chosen from $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers.

7. The composition according to claim 6, wherein the at least one water-insoluble oxygenated organic compound is chosen from ethylene glycol monostearate and distearate, pentaerythrityl monooleate, sorbitan tristearate, glyceryl dioleate, fatty esters, amides and ethers of ethylene glycol or of propylene glycol, distearyl ether, stearyl alcohol, behenyl alcohol and cetylstearyl alcohol.

8. The composition according to claim 1, wherein the amount of the at least one water-insoluble oxygenated organic compound in the composition ranges from greater than 30% to 60% by weight of the composition.

9. The composition according to claim 1, wherein the composition comprises water in an amount ranging from 20% to 68% by weight relative to the total weight of the composition.

10. The composition according to claim 1, further comprising:
anionic, nonionic, cationic and amphoteric surfactants comprising at least one linear or branched $C_6$-$C_{22}$ alkyl chain;
amphiphilic polymers; and
thickening polymers.

11. The composition according to claim 10, wherein said amphiphilic polymers are chosen from water-soluble or water-dispersible amphiphilic block copolymers, and associative polymers bearing on their main chain oxyethylenated or non-oxyethylenated, telechelic or grafted $C_6$-$C_{22}$ alkyl and/or aryl groups, of cationic, anionic, amphoteric or nonionic charge.

12. The composition according to claim 10, wherein said thickening polymers are chosen from crosslinked acrylic polymers and natural or modified polysaccharides.

13. The composition according to claim 1, further comprising at least one additive chosen from sequestrants; chemical hydrogen peroxide stabilizers; fragrances; antifoams; cationic or amphoteric substantive polymers; water-soluble or water-insoluble conditioning polymers, and chelating agents.

14. The composition according to claim 1, wherein the pH of the composition ranges from 2 to 12.

15. The composition according to claim 14, wherein the pH of the composition ranges from 3 to 6.

16. A process for bleaching human keratin fibers, comprising:
applying a ready-to-use oxidizing composition to the area of the human keratin fibers to be bleached;
leaving the ready-to-use oxidizing composition to act for a leave-on time that is sufficient to obtain the desired bleaching; and
removing the composition by rinsing with water, followed by washing with a shampoo and then optionally drying;
wherein the ready-to-use oxidizing composition comprises in a cosmetically acceptable medium:
(a) at least one oxidizing agent;
(b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
(c) at least 20% by weight of water relative to the total weight of the composition.

17. A process for stripping dyed human keratin fibers, comprising:
applying a ready-to-use oxidizing composition to the area where the dyed human keratin fibers are to be stripped;
leaving the ready-to-use oxidizing composition to act for a leave-on time that is sufficient to obtain the desired stripping; and
removing the ready-to-use composition by rinsing with water, followed by washing with a shampoo and then optionally drying;
wherein the ready-to-use oxidizing composition comprises in a cosmetically acceptable medium:
(a) at least one oxidizing agent;
(b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
(c) at least 20% by weight of water relative to the total weight of the composition.

18. A process for the oxidation dyeing of human keratin fibers, comprising:
- applying a dye composition to the keratin fibers;
- wherein the dye composition comprises, in a support that is suitable for dyeing keratin fibers, at least one oxidation dye precursor and a ready-to-use oxidizing composition;
- wherein the ready-to-use oxidizing composition comprises in a cosmetically acceptable medium:
  - (a) at least one oxidizing agent;
  - (b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
  - (c) at least 20% by weight of water relative to the total weight of the composition;
- wherein the ready-to-use oxidizing composition is applied before or after the application of the dye composition, or is mixed with the dye composition;
- leaving the compositions to act for about 1 to 60 minutes; and
- rinsing the fibers, washing with shampoo and then optionally rinsing and drying.

19. A process for the lightening direct dyeing of human keratin fibers, comprising:
- applying a dye composition to the keratin fibers;
- wherein the dye composition comprises, in a support that is suitable for dyeing keratin fibers, at least one direct dye and a ready-to-use oxidizing composition;
- wherein the ready-to-use oxidizing composition comprises in a cosmetically acceptable medium:
  - (a) at least one oxidizing agent;
  - (b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
  - (c) at least 20% by weight of water relative to the total weight of the composition;
- wherein the ready-to-use oxidizing composition is applied to the keratin fibers before or after the application of the dye composition, or is mixed with the dye composition;
- leaving the compositions to act for about 1 to 60 minutes; and
- rinsing the fibers, washing with shampoo, optionally rinsing again, and drying.

20. A process for permanently reshaping human keratin fibers, comprising:
- applying a reducing composition to the keratin fibers to be reshaped, placing the keratin fibers under mechanical tension before, during or after the application of the reducing composition;
- leaving the keratin fibers on which the reducing composition has been applied to stand;
- optionally rinsing the keratin fibers with an aqueous composition;
- applying a ready-to-use oxidizing composition to the keratin fibers, wherein the ready-to-use oxidizing composition comprises in a cosmetically acceptable medium:
  - (a) at least one oxidizing agent;
  - (b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
  - (c) at least 20% by weight of water relative to the total weight of the composition;
- leaving the keratin fibers on which the oxidizing composition has been applied to stand; and then
- rinsing the keratin fibers with an aqueous composition.

21. A method for dyeing, permanently reshaping, bleaching, lightening or dyeing keratin fibers, comprising applying to the keratin fibers a ready-to-use oxidizing composition comprising in a cosmetically acceptable medium:
- (a) at least one oxidizing agent;
- (b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
- (c) at least 20% by weight of water relative to the total weight of the composition.

22. A multi-compartment kit for dyeing, permanently reshaping or bleaching keratin fibers, comprising:
- at least two compartments; wherein
- at least one first compartment comprises either at least one direct dye, or at least one oxidation dye composition, or a reducing composition, or a first oxidizing composition;
- and at least one second compartment comprises a ready-to-use oxidizing composition, wherein the ready-to-use oxidizing composition comprises in a cosmetically acceptable medium:
  - (a) at least one oxidizing agent;
  - (b) greater than 30% by weight, relative to the total weight of the composition, of at least one water-insoluble oxygenated organic non-dyeing compound chosen from $C_8$ to $C_{40}$ fatty alcohols, $C_8$ to $C_{40}$ fatty acid esters, $C_8$ to $C_{40}$ fatty acid amides, $C_8$ to $C_{40}$ fatty alcohol esters, $C_8$ to $C_{40}$ fatty alcohol amides, and $C_8$ to $C_{40}$ fatty alcohol ethers; and
  - (c) at least 20% by weight of water relative to the total weight of the composition.

* * * * *